United States Patent [19]

Watanabe

[11] Patent Number: 5,075,551
[45] Date of Patent: Dec. 24, 1991

[54] INFRARED ABSORPTION ENHANCED SPECTROSCOPIC APPARATUS

[75] Inventor: Atsuo Watanabe, Kanagawa, Japan

[73] Assignee: Fuji Electric Co., Ltd., Kanagawa, Japan

[21] Appl. No.: 666,221

[22] Filed: Mar. 7, 1991

[30] Foreign Application Priority Data

Mar. 12, 1990 [JP] Japan .................................. 2-57992
Jul. 11, 1990 [JP] Japan ................................ 2-183376

[51] Int. Cl.⁵ ............................................ G01N 21/00
[52] U.S. Cl. ..................................... 250/341; 250/353; 356/36; 356/445
[58] Field of Search ............... 250/341, 353, 338.1, 250/304; 356/36, 38, 445

[56] References Cited

U.S. PATENT DOCUMENTS

| | | | |
|---|---|---|---|
| 3,604,927 | 9/1971 | Hirschfeld | 356/244 |
| 3,975,084 | 8/1976 | Block | 250/574 |
| 4,181,441 | 1/1980 | Noller | 250/573 |
| 4,490,618 | 12/1984 | Cielo | 250/571 |
| 4,602,869 | 7/1986 | Harrick | 356/445 |
| 4,818,710 | 4/1989 | Sutherland | 356/445 |
| 4,844,613 | 7/1989 | Batchelder et al. | 356/445 |
| 4,857,273 | 8/1989 | Stewart | 350/96.15 |
| 4,889,427 | 12/1989 | Van Veen et al. | 356/445 |

FOREIGN PATENT DOCUMENTS 2173895 10/1986 United Kingdom .

OTHER PUBLICATIONS

Rothenhäusler, Benno, "Surface-Plasmon Microscopy", Apr. 14, 1988, Nature, vol. 332, pp. 615-617.
Hatia, A. et al, "Observation of the Enhanced Infrared Absorption of p-Nitrobenzoate on AG Island Films with an ATR Technique", Appl. Phys. A29, pp. (71-75), 1982.
Hatia, A., "Infrared Absorption Enhancement of Monolayer Species on Thin Evaporated Ag Films by Use of a Kretchmann Configuration: Evidence of Two Types of Enhanced Surface Electric Fields", Appl. Phys. A35, pp. 135-140 (1984).
Ishino, Yuichi et al., "Grazing Angle Metal-Overlayer Infrared ATR Spectroscopy", Appl. Spectroscopy, vol. 42, No. 7, pp. (1296-1302) (1988).
Bell, Robert J. et al, "Introductory Theory for Surface Electromagnetic Wave Spectroscopy", Surface Science, 48, pp. 253-287 (1975).
"Excitation of Nonradiative Surface Plasma Waves in Silver by the Method of Frustrated Total Reflection", by Andreas Otto, Zeitschrift Fur Physik, 216, pp. 398-410 (1968).
"Die Bestimmung Optischer Konstanten von Metallen durch Anregung von Oberflachenplasmaschwingungen", Z. Physik, 241, pp. 313-324 (1971), by Erwin Kretschmann.

Primary Examiner—Carolyn E. Fields
Assistant Examiner—Drew A. Dunn
Attorney, Agent, or Firm—Finnegan, Henderson, Farabow, Garrett and Dunner

[57] ABSTRACT

An infrared absorption enhanced spectroscopic apparatus includes a reflecting face of a high refractive-index prism shaped to retain a metal layer, such as a solid plasma of aluminum, in such a way that it can be pressed uniformly against the reflecting face of the prism. Both entrance and exit faces of the prism are made sufficiently flat to minimize the scattering of infrared light when it is admitted into or emerges from the prism. A thin layer (approximately 500 Å) of a sample of interest is deposited on the surface of the metal layer, which overlays a flexible support member, such as a polyethylene terephthalate film having a thickness of approximately 50 μm. The apparatus has a mechanism by which the metal layer and thin sample layer can be pressed into intimate contact with the reflecting face of the prism. The apparatus also has a mechanism for adjusting the angle of incidence of infrared light with respect to the reflecting face of the prism.

19 Claims, 8 Drawing Sheets

INFRARED ABSORPTION ENHANCED SPECTROSCOPIC APPARATUS

BACKGROUND OF THE INVENTION

1. Field of the Invention

This invention relates to an infrared absorption enhanced spectroscopic apparatus. More particularly, this invention relates to an infrared absorption enhanced spectroscopic apparatus in which a thin layer of a sample to be analyzed is placed in the gap between a reflecting face of a high refractive-index prism that also has an entrance face and an exit face and a metal as solid plasma comprises free electrons.

2. Description of the Related Art

Materials such as metals that permit electrons to move freely may be regarded as solid plasmas. Surface electromagnetic waves (surface plasmons) can exist in the neighborhood of the surfaces of such solid plasmas. Photoexcitation of surface electromagnetic waves can be achieved by using either a high refractive-index prism or a diffraction grating formed on the surface of a metal.

FIG. 5 is a sketch illustrating the concept of surface electromagnetic wave excitation proposed by Andreas Otto in "Excitation of Nonradiative Surface Plasma Waves in Silver by the Method of Frustrated Total Reflection", Zeitschrift for Physik, 216, pp. 398–410 (1968). Shown by 1 is a prism having a high refractive index $n_p$ that is placed on top of a metal 3 having a dielectric constant of $a(\omega)$ with a gap 2 of a dielectric constant of $a(\omega)$ being formed between the two elements; $\omega$ is the angular frequency of light and dielectric constants $\theta$ and $\epsilon$ are each a function of $\omega$. Incident light 4 is reflected totally by the bottom surface of the prism 1. The reflected light 5 travels through the prism. The wave number $k_p$ (the inverse of the wavelength) of the light travelling through the prism is expressed by $\eta_p \cdot \omega/c$ (c is the velocity of the light). If $k_p \text{SIN}\theta$, or the component of $k_p$ in the x-direction is equal to the wave number of surface electromative waves to be excited, $k_x$, then surface electromagnetic waves 6 are excited to occur on the surface of the metal 3.

The wave number, $k_x$, of surface electromagnetic waves 6 can be correlated to the angular frequency, $\omega$, of the light in terms of dispersion by the following equation:

$$k_x = \omega/c \sqrt{\epsilon \eta / (\epsilon + \eta)} \quad (1)$$

With electromagnetic waves of comparatively low frequencies such as infrared light, the absolute value of the dielectric constant of a metal $|\epsilon|$ is far greater than the absolute values of the dielectric constants of common dielectrics. Therefore, equation (1) can be approximated as follows:

$$k_x = \omega/c \sqrt{\eta} \quad (2)$$

This indicates that surface electromagnetic waves of low frequencies behave like photons that are guided through a gap by a good electric conductor.

By the principle described above, infrared light can be transmitted through a thin layer of a sample on the surface of a metal in a direction parallel to the surface of the thin layer, and an improved sensitivity of analysis can be obtained if the infrared light is permitted to pass through the thin-film sample over an increased distance.

Surface electromagnetic waves have been studied for many years and methods of exciting surface electromagnetic waves using high refractive-index prisms have been proposed not only by Otto, supra, but also by Erwin Kretschmann in "Die Bestimmung optischer Konstanten von Metallen dutch Anregung von Oberflächenplasmaschwingungen", Z. Physik, 241, pp. 313–324 (1971).

Spectroscopy with surface electromagnetic waves in the strict sense of the term would typically involve the use of two spaced prisms for measuring the ratio of the intensity of light propagating through the surfaces of the gap to the intensity of incident light. However, it has been verified that surface electromagnetic waves can also be excited by using a single prism in the method of Otto or Kretschmann. It is possible to increase the sensitivity of analysis by enhancing the absorption of infrared light by a thin layer of sample deposited on the surface of a metal, which infrared light has been passed in a direction parallel to the surface of the thin layer.

Various attempts have been made in order to realize this possibility. See, for example, A. Hatta, T. Ohshima and W. Suetaka, "Observation of the Enhanced Infrared Absorption of p-Nitrobenzoate on Ag Island Films with an ATR Technique", Appl. Phys., A29, pp. 71–75 (1982) and A. Hatta, Y. Suzuki and W. Suetaka, "Infrared Absorption Enhancement of Monolayer Species on Thin Evaporated Ag Films by Use of a Kretchmann Configuration: Evidence of Two Types of Enhanced Surface Electric Fields", Appl. Phys., A35, pp. 135–140 (1984). Suetaka et.al. observed enhanced infrared absorption by thin films deposited on evaporated silver films on the flat surface of a hemicylindrical germanium prism. Ishida et.al., Yuichi Ishino and Hatsuo Ishida, in "Grazing Angle Metal-Overlayer Infrared ATR Spectroscopy", Applied Spectroscopy, Vol. 42, No. 7, pp. 1296–1302 (1988), described the use of a germanium prism having both a flat entrance face and a flat exit face so as to provide an incident angle of 75° and observed that infrared absorption could be enhanced by evaporating silver on the surface of a thin layer of sample that was deposited on the reflecting face of the prism.

In all of these methods, metal layers are formed by evaporation. Special equipment such as a vapor deposition system are necessary if one wants to apply those methods to routine analyses. Further, the two methods of Suetaka et.al. enhance the infrared absorption by using island Ag particles. Even if the involvement of surface electromagnetic waves is taken into account, the need to use a particular metallic material (Ag) and deposit it in the form of island films is a very strict limitation on the use of those methods by ordinary analysts.

Another paper that may be cited as a general reference that describes the background of the present invention with respect to the use of surface electromagnetic waves in spectroscopy is Robert J. Bell, R. N. Alexander, Jr., C. A. Ward and I. L. Tyler, Introductory Theory For Surface Electromagnetic Wave Spectroscopy", Surface Science, 48, pp. 253–287 (1975).

SUMMARY OF THE INVENTION

The present invention has been achieved under these circumstances and has as an object providing an infrared absorption enhanced spectroscopic apparatus that performs measurements by the principle described above, that permits a metal surface, an overlying thin layer of sample and a high refractive-index prism to be readily set in such a way that their relative positions can be measured, that permits the angle of incident infrared light to be readily adjusted in such a way that the wave number of infrared light travelling through the prism in a direction parallel to its bottom surface becomes equal to the wave number of surface electromagnetic waves to be excited, and that has an optical system which causes a sufficiently small loss of infrared light to achieve a satisfactory S/N ratio.

Additional objects and advantages of the invention will be set forth in part in the description which follows, and in part will be obvious from the description, or may be learned by practice of the invention. The objects and advantages of the invention may be realized and attained by means of the combinations pointed out in the appended claims.

The objects of the present invention can be attained by an infrared absorption enhanced spectroscopic apparatus in which using a high refractive-index prism, surface electromagnetic waves are excited to occur on the surface of solid plasma such as a metal that comprises free electrons, the excited surface electromagnetic waves being permitted to behave in such a way that incident infrared light will travel in plane through a thin layer deposited on the surface of the solid plasma, whereby the absorption of the light by the thin layer is enhanced to increase the sensitivity of analysis, which apparatus is characterized in that: (i) the reflecting face of the high refractive-index prism has a shape that is capable of retaining the metal as a solid plasma in such a way that it can be pressed uniformly against the reflecting face of the prism and both the entrance and exit faces of the prism are made sufficiently flat to minimize the divergence of infrared light when it is admitted into or emerges from the prism;

(ii) the thin layer to be analyzed is deposited on the surface of the metal evaporated in a thickness of approximately 500 Å on a flexible support member;

(iii) the apparatus has a mechanism by which the evaporated metal film having the thin layer of interest deposited thereon can be pressed into intimate contact with the reflecting face of the prism; and (iv) the apparatus also has an adjusting mechanism that is capable of changing the angle of incidence of infrared light with respect to the reflecting face of the prism.

BRIEF DESCRIPTION OF THE DRAWINGS

The accompanying drawings, which are incorporated in and constitute a part of the specification, illustrate a preferred embodiment of the invention and, together with the general description above and detailed description below, explain the principles of the invention.

DESCRIPTION OF THE PREFERRED EMBODIMENTS

Figure 1:
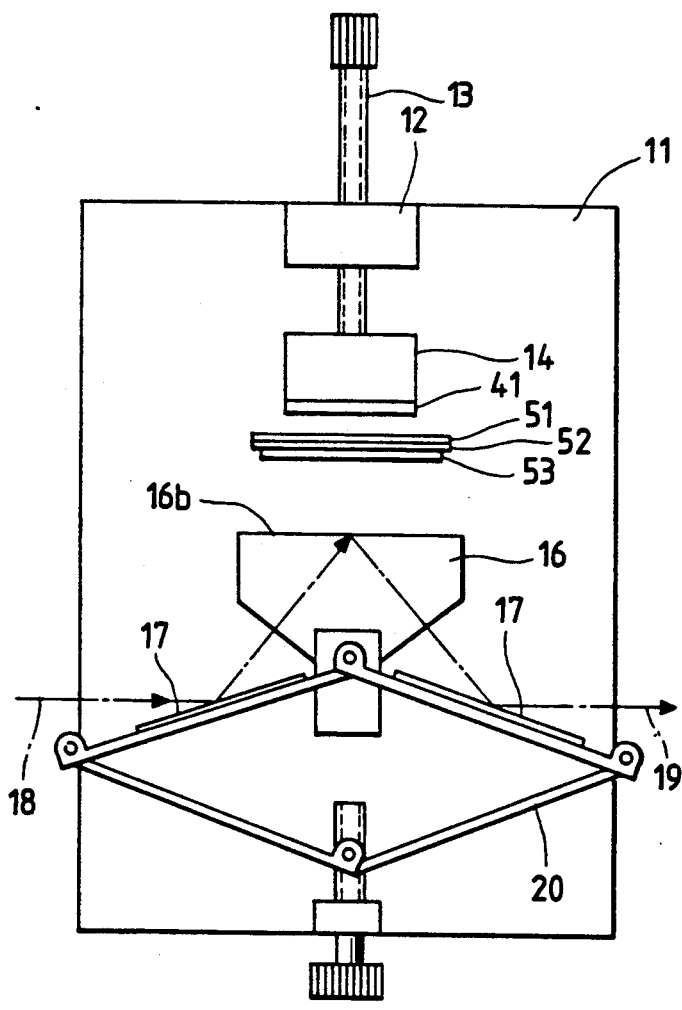
FIG. 1 is a front view showing an infrared absorption enhanced spectroscopic apparatus according to an embodiment of the invention.

Reference will now be made in detail to the present preferred embodiments of the invention as illustrated in the accompanying drawings.

The support member in the infrared absorption enhanced spectroscopic apparatus of the present invention preferably satisfies the requirement for being either elastic or flexible or both and may be exemplified by a polyethylene terephthalate film having a thickness of about 50 $\mu$m or a polyester film having a thickness of about 75 $\mu$m. It should, however, be noted that the shape of the support member is in no way limited to a film as long as it satisfies the requirement for being either elastic or flexible or both, and facilitates permitting the film of a metal as a solid plasma to be pressed against the reflecting face of the prism as uniformly as possible.

The metal as a solid plasma is preferably aluminum. An aluminum layer evaporated on the support member in a thickness of about 500 Å can be used as a medium for excitation of surface electromagnetic waves.

In light of the objects of the present invention, the prism in the infrared absorption enhanced spectroscopic apparatus preferably has the edges of sides of the reflecting face chamfered or cutoff so that the width of the reflecting face is reduced in exact correspondence with the width of the area in which the sample to be analyzed is deposited on the surface of the metal layer.

The dielectric constant of a metal is expressed by $\delta = \delta_1 + i\delta_2$ (where i denotes an imaginary number) and its absolute value increases at lower frequencies. In the infrared region, $$-\epsilon_1 > \eta_1 \quad (3)$$

and the dispersion of excited surface electromagnetic waves can be approximated by equation (2), which is reasonably satisfied by metals that satisfy equation (3).

Equation (2) can be expressed as follows using the complex refractive index of a thin film:

$$k_x = \omega/c(n_s - ik_s) \quad (4)$$

where $(n_s - ik_s)$ represents the complex refractive index of a sample in thin film form; $n_s$ is the real part of the complex refractive index; and $k_s$ is its imaginary part and is sometimes referred to as an attenuation factor.

The light travelling through a prism (refractive index: $n_p$) has a wave number $k_p$. Let us now consider the condition that should be satisfied for the component of wave number in a direction parallel to the bottom surface of the prism ($k_p \sin\theta$) to become equal to the wave number of excited surface electromagnetic waves. Assuming the equality of the two wave numbers, $$k_p \sin\theta = n_p(\omega/c)\sin\theta$$
$$= \omega/c(n_s - iK_s).$$

By rearrangement, we obtain:

$$\sin\theta = \frac{1}{n_p}(n_s - ik_s). \quad (5)$$

If $k_s > n_s$, the following approximation will hold:

$$\sin\theta \approx n_s/n_p \quad (6)$$

With most ordinary samples to be analyzed, $n_s$ is approximately 1.5. Hence, if the prism has a refractive index ($n_p$) of 4 as in the case of germanium, $\theta$ is set to about 22.5° and if the prism has a refractive index of 2.4 as in the case of KRS-5, $\theta$ is set to about 39°, with fine adjustments of the incident angle being effected in accordance with the specific type of sample to be analyzed.

It is practically impossible to reduce the gap between the reflecting face of a high refractive-index prism and the flat surface of a metal to such a small level that surface electromagnetic waves can be excited on the metal surface by evanescent waves from the prism surface. In order to insure that effective surface electromagnetic waves are excited on the flat metal surface by means of evanescent waves (i.e., electromagnetic waves that diminish exponentially) from the surface of the high refractive-index prism, the reflecting face of the prism must be brought sufficiently close to the flat metal surface to produce a gap on the order of 0.1 μm at its maximum point, even if the surface electromagnetic waves to be excited have wavelengths in the infrared region. At the same time, both the prism and the metal surface must be polished to have a flatness on the order of 0.1 μm.

Even if this level of flatness is attained, there is one more requirement to be satisfied and that is for the absence of any particles with a diameter of 0.1 μm or more that may be deposited on either the prism surface or the metal surface. Even a single particle of this size will be sufficient to separate the two surfaces by a distance of 0.1 μm or more.

In the process of fabricating VLSI semiconductors, cleanliness of that order is usually attained but this is only possible in a closely controlled clean environment. In order to insure that two surfaces are in contact with each other within a tolerance of 0.1 μm over an area of at least several tens of percent of the total area in less clean environments, one surface must be flexible enough to conform to the other.

The prism is usually made of a crystal and cannot be expected to be flexible. Most metals are also hard and flexibility cannot be expected. However, a thickness of less than 1,000 angstroms is sufficient for metals to play an optical role. Hence, flexible plastic films having a metal evaporated on their surface in a thickness of say 500 Å, for example, will behave optically in the same manner as semi-finite metal surfaces.

A clearance on the order of 0.1 μm between the reflecting face of the prism and the metal surface when they are placed in contact with other can be attained by pressing the reflecting face into intimate contact with a metal evaporated in a thickness of approximately 500 Å on a flexible film. If the flexible film is so thin that the compression surface that is to exert a pressure from the back side of the film can cause a deteriorative effect, a cushion layer may be provided adjacent the compression surface so that a uniform pressure is applied to the film surface.

When the apparatus of the present invention is to be used with a spectrophotometer, the sample cell in which the sample and various accessories for measurement are to be placed typically has a predetermined optical path, with the focus being positioned at the center of the optical path in the sample cell. Hence it is also desired that the entrance and exit ports of the apparatus of the present invention are symmetrical with each other, providing a focus at the reflecting point of the prism. The apparatus of the present invention adopts an optical system that permits the incident angle to be varied over a certain range and that allows the incident light to be focused at the reflecting point of the prism.

Figure 2:
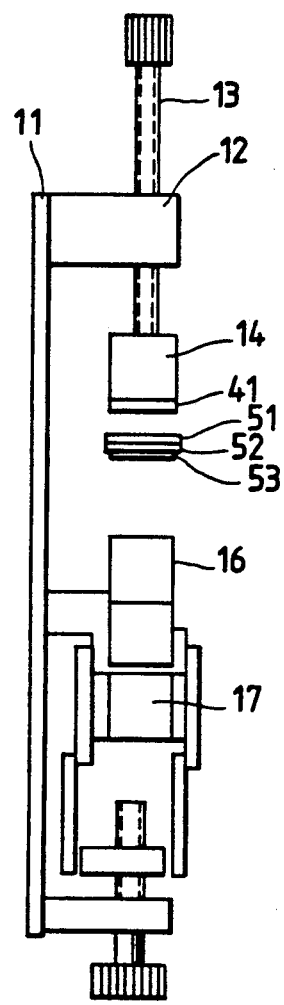
FIG. 2 is a side view of the apparatus shown in FIG. 1.

FIG. 1 is a front view of an infrared absorption enhanced spectroscopic apparatus according to an embodiment of the present invention, and FIG. 2 is a side view of the same apparatus. In FIGS. 1 and 2, shown by 11 is a base plate, 12 is a press screw holder, 13 is a press screw, 14 is a compression block, 41 is a cushion, 51 is a polyethylene terephthalate (PET) film, 52 is an evaporated aluminum film, 53 is a sample to be analyzed, 16 is a high refractive-index prism, 17 is a reflector, 18 is incident light, 19 is emerging light, and 20 is a mechanism for adjusting the incident and exit angles.

The construction of the apparatus shown in FIGS. 1 and 2 is briefly described below. The base plate 11 serves as a support for the principal part of the apparatus. An adjusting mechanism is positioned outside the base plate 11 and brings the optical axes of incident light 18 and emerging light 19 into alignment with the optical axis of an external device. The incident light is directed into the apparatus by means of reflector 161 and the reflected light reflected off of reflective 163 is p-polarized by means of a polarizer 164 positioned on the optical axis of the reflected light (see FIG. 9(a)). Analysis with the apparatus under discussion is usually performed on p-polarized light.

Press screw holder 12, press screw 13 and compression block 14 combine to work as a mechanism by which film 51 having an evaporated metal layer 52 that is overlaid with the thin film of sample 53 is pressed against the reflecting face of the high refractive-index prism 16. The film 51 which supports the sample 53 is made of a plastic material such as PET and has a metal such as aluminum evaporated thereon to form the metal layer 52. The reflecting face of the prism 16 is sufficiently smooth to achieve intimate contact with the "flexible" evaporated metal surface 52. The prism is so shaped that light is admitted into and reflected by the crystal at an angle of approximately 22.5 degrees if the prism has a refractive index of 4, and at approximately 39 degrees if the prism has a refractive index of 2.4.

The reflector 17 permits horizontal incident light to pass through the crystal at a desired angle and to exit therefrom again horizontally after refraction by a certain angle. The angles at which light falls on and emerges from the crystal can be adjusted by means of the mechanism 20.

As will be understood from the above description, the apparatus will be operated as follows: the press screw 13 is turned to lower the compression block 14 and cushion 41 so that the PET film 51, evaporated aluminum film 52 and sample 53 are pressed en masse against the reflecting face of the prism 16, and the incident angle of light 18 is adjusted by the mechanism 20.

An example of analysis with the apparatus shown in FIGS. 1 and 2 is described below.

A polyester film 75 $\mu$m thick having aluminum evaporated in a thickness of approximately 500 Å was used as a substrate. An alkyd resin was coated on the aluminum layer in a thickness of 100 Å. The alkyd resin was dissolved in an amount of 1 wt % in toluene and a predetermined volume of the solution was metered with a microsyringe and spread uniformly over the surface of the aluminum layer.

Figure 3:
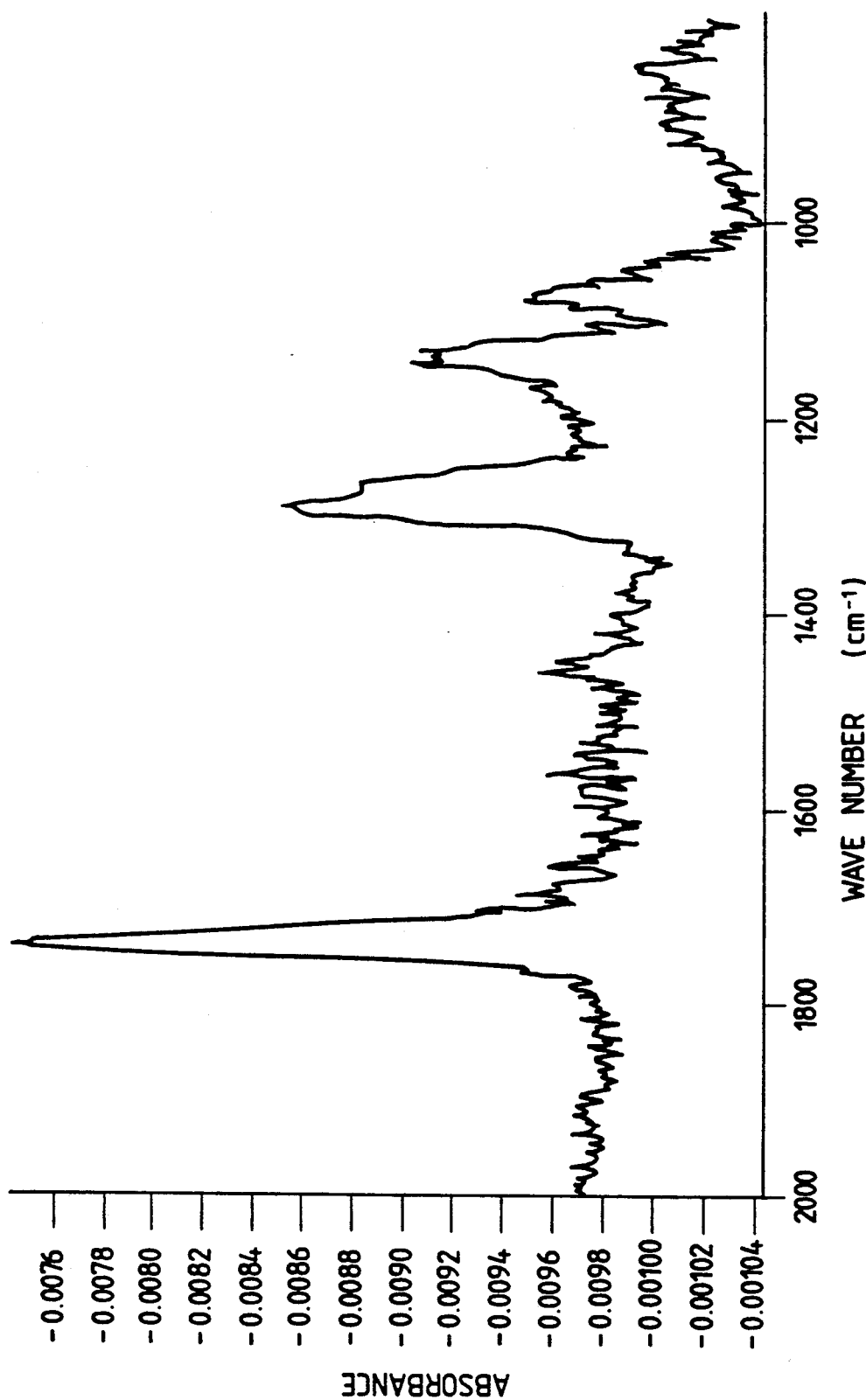
FIG. 3 is a spectrogram that shows the result of an analysis by a typical prior art specular reflection method.
Figure 4:
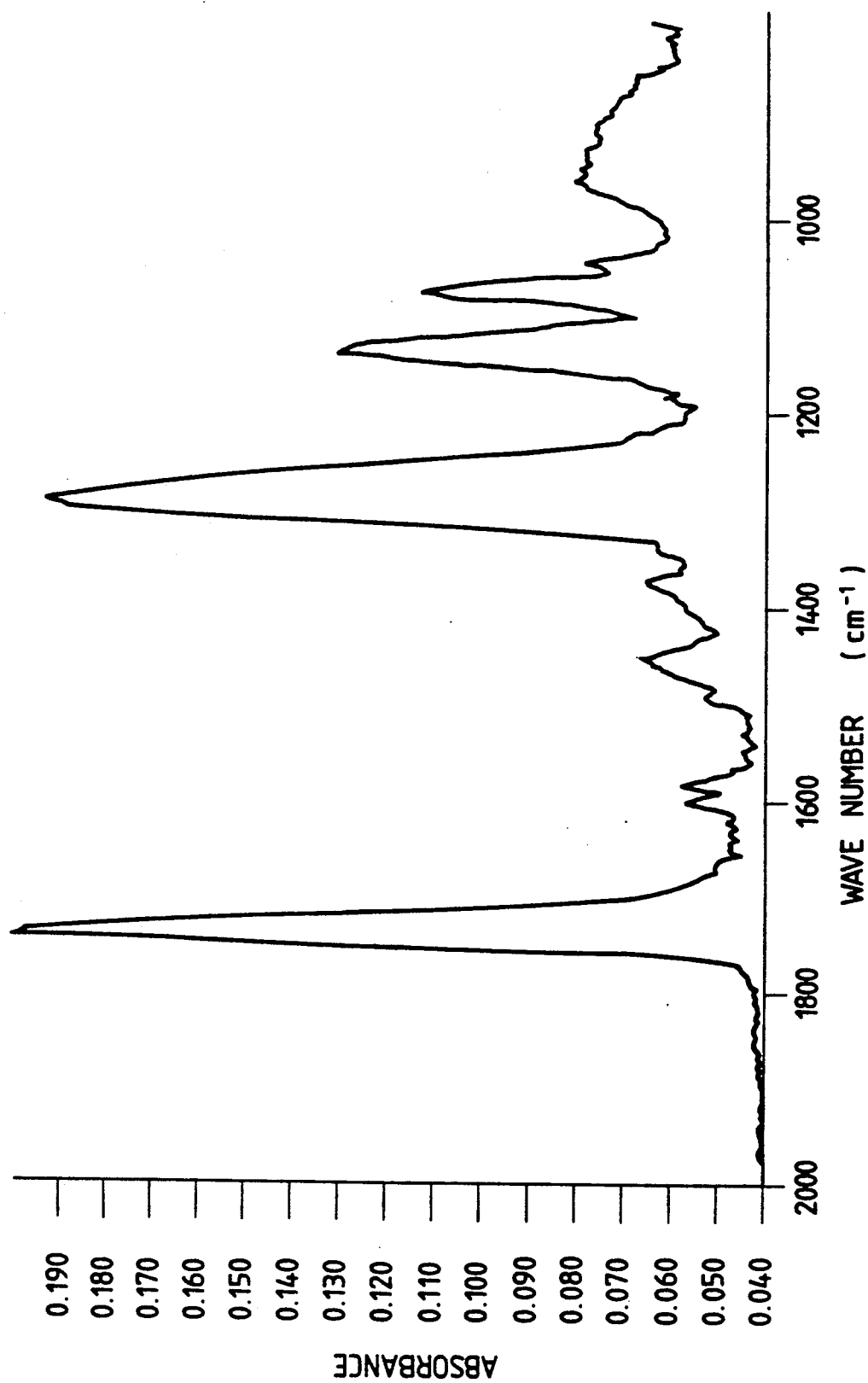
FIG. 4 is a spectrogram that shows the result of an analysis using the apparatus of the present invention.
Figure 5:
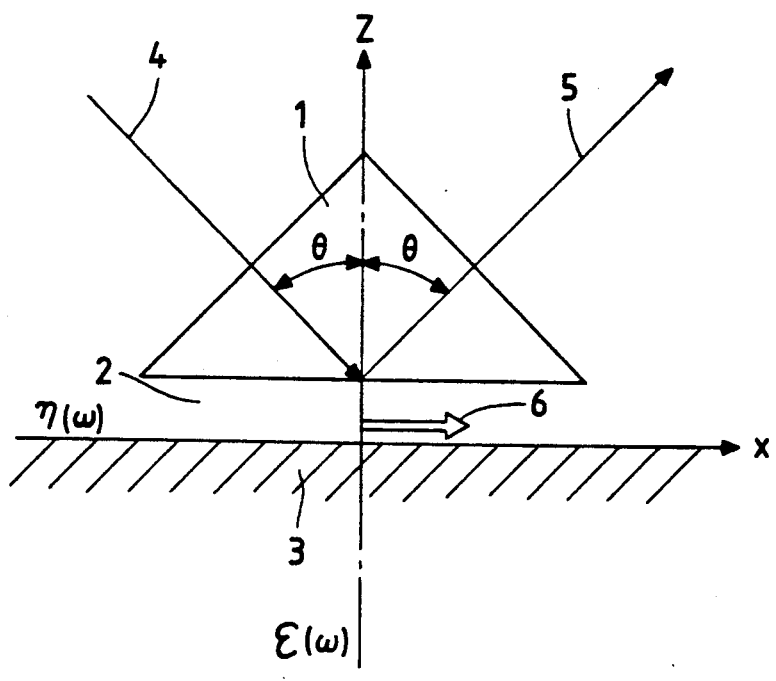
FIG. 5 (prior art) is a sketch illustrating the concept of surface electromagnetic wave excitation.

The thus prepared sample was measured by a conventional specular reflection method using a 4 cm$^{-1}$, 32-scan DTGS detector. The spectrum obtained is shown in FIG. 3. The same sample was measured under the same conditions using the apparatus of the present invention and the spectrum obtained is shown in FIG. 4.

Obviously, the spectrum obtained with the apparatus of the present invention has less noise and even small peaks can be clearly recognized. On the other hand, the spectrum obtained by a conventional specular reflection method has much noise and the presence of small peaks is not discernible. A maximum absorption peak occurs at 1734 cm$^{-1}$ or thereabout in both spectra. A comparison of absorbance shows that the peak occurs at 1734 cm$^{-1}$. In FIG. 4 a peak is 65 times as high as the corresponding peak in FIG. 3. Hence, if absorbance is the only factor in the determination of sensitivity, the apparatus of the present invention increases the sensitivity of analysis by a factor of 65.

As described above, infrared absorption can be effectively enhanced if a metal layer as a medium for exciting surface electromagnetic waves is evaporated on a flexible plastic film. The use of plastic films as the support of metal layers provides further advantage.

Materials that can be used as the support of metal layers are in no way limited to plastic films and any support can be used as long as it is reasonably elastic or flexible and if it is capable of assisting in permitting the thin metal layer with a deposited sample layer to be pressed against the reflecting face of the prism as uniformly as possible.

Examples of metal supports other than plastic films are described below. As is often practiced, a sample of interest is partitioned into components by liquid chromatographic separation. In this case, a thin metal layer is evaporated on a film in the form of elongated tape. When fractions of the sample as it is separated by the liquid chromatography are successively deposited on the tape film, the separated components can be analyzed very easily in accordance with the order of their separation using the infrared absorption enhanced spectroscopic technique of the present invention.

Figure 6A:
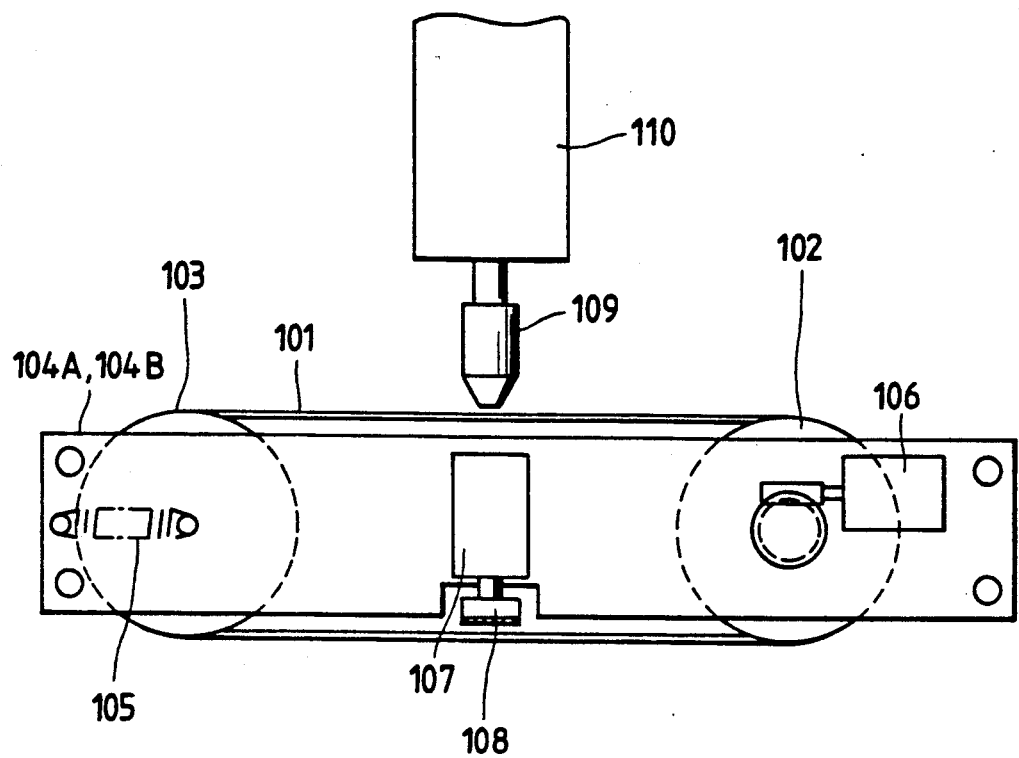
FIG. 6(a) is a front view of one example of a tape cassette of a film in tape form as a support member on which components of a sample to be measured are successively deposited as they are separated by a liquid chromatography.
Figure 6B:
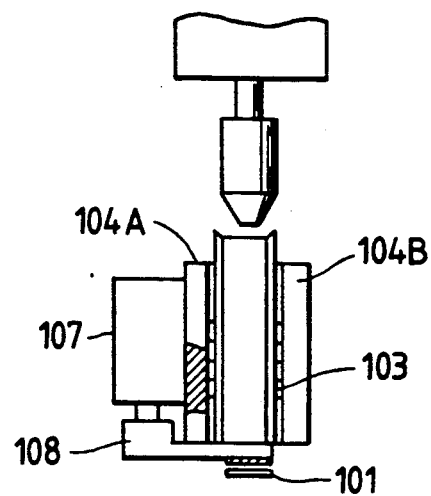
FIG. 6(b) is a side view of the apparatus shown in FIG. 6(a)

FIGS. 6(a) and 6(b) are a front and a side view, respectively, of an example of a tape cassette of a film in tape form as a support member on which components of a sample to be measured are successively deposited as they are separated by the liquid chromatography. Referring to FIG. 6(a), the numeral 101 represents a continuous flexible PET film strip. The tape 101 is wound onto two pulleys 102 and 103, each of which is supported rotatably by side plates 104A and 104B, with the axes of the respective pulleys extending parallel to each other. Stated more specifically, the pulley 102 has its longitudinal axis fixed whereas the longitudinal axis of the pulley 103, which is used to apply tension to the tape 101 as will be described below, is capable of translational movement in the horizontal direction over a small range.

A motor indicated by 106 is secured to the side plate 104A and drives the pulley 102 to rotate via a worm and a wormwheel (not labelled with numerals). A spring 105 urges the pulley 103 toward the left so that it pulls the tape 101 in the same direction.

A nozzle 109 connected to the outlet of a column 110 is positioned above the upper tape 101 in proximity to the outer surface of the center of its straight portion. A compression block 108 is positioned above the lower position of tape 101, in proximity to the inner surface of the center of its straight portion. As shown in FIG. 6B, the compression block 108 is an L-shaped metal element that is secured to the output shaft of an actuator 107 fixed to the side plate 104A. An elastic member that is hatched is attached to the underside of the compression block at an end portion.

Components of the sample separated in the column 110 are discharged through the nozzle 109 at a given speed together with the mobile phase carrier and are successively deposited at different positions on the outer surface of the center of the straight portion of the upper tape 101 being fed at a constant speed. Each of the deposited components is carried by the tape 101 to reach the center of the straight portion of the lower portion of the tape, where it is pressed into intimate contact with the reflecting face of the prism (not shown) by means of the compression block 108 being driven downward with the actuator 107. Prior to the pressing operation, the mobile phase carrier is evaporated to leave only the component of interest intact on the tape 101.

Figure 7A:
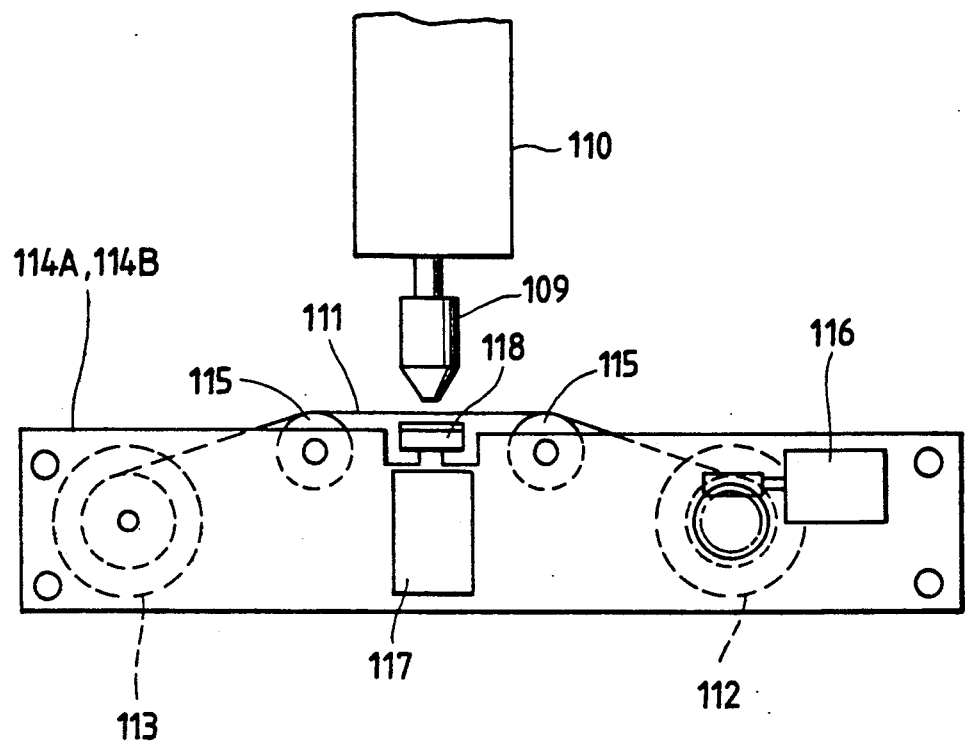
FIG. 7(a) is a front view of another example of the cassettes of a film tape on which the components of a sample to be measured are successively deposited as they are separated by a liquid chromatography.
Figure 7B:
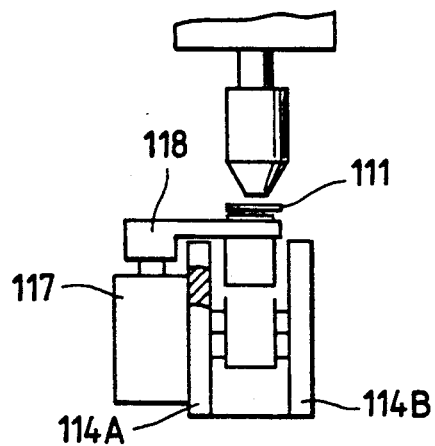
FIG. 7(b) is a side view of the apparatus shown in FIG. 7(a)

FIGS. 7(a) and 7(b) are a front view and a side view, respectively, that show another example of the cassette of a film tape on which the components of a sample to be measured are successively deposited as they are separated by the liquid chromatography. Referring to FIG. 7(a), the numeral 111 represents a flexible PET film strip that is wound onto a reel 113 for storage before analysis. The tape can be wound up onto a takeup reel 112.

Each of the reels 112 and 113 is supported rotatably by side plates 114A and 114B, with the axes of the respective reels extending parallel to each other. A motor indicated by 116 is secured to the side plate 114A and drives the reel 112 to rotate clockwise via a worm and a wormwheel (not labelled with numerals), whereby the tape 111 is taken up by the reel 112. The tape 111 as it is rewound from the reel 113 to be taken up by the reel 112 is properly positioned by means of two intermediate pulleys 115.

A nozzle 109 connected to the outlet of column 110 is positioned above the tape 111 in proximity to the outer surface of the center of its straight portion. A compression block 118 is positioned below the tape 111 in proximity to the inner surface of the center of its straight portion. As shown in FIG. 7(b), the compression block 118 is an L-shaped metal element that is secured to the output shaft of an actuator 117 fixed to the side plate 114A. An elastic member that is hatched is attached to the top of the compression block at an end portion.

Components of the sample separated in the column 110 are discharged through the nozzle 109 at a given speed together with the mobile phase carrier and are successively deposited at different positions on the outer surface of the center of the straight portion of the tape 111 being fed at a constant speed. Each of the deposited components on the tape 111 is pressed into intimate contact with the reflecting face of the prism (not shown) by means of the compression block 118 which is driven upward with the actuator 117. The device shown in FIG. 7(a) which is used to have the separated components of the sample deposited at different positions on the tape, is set in an infrared spectrometer, with the device being turned upside down.

Figure 8A:
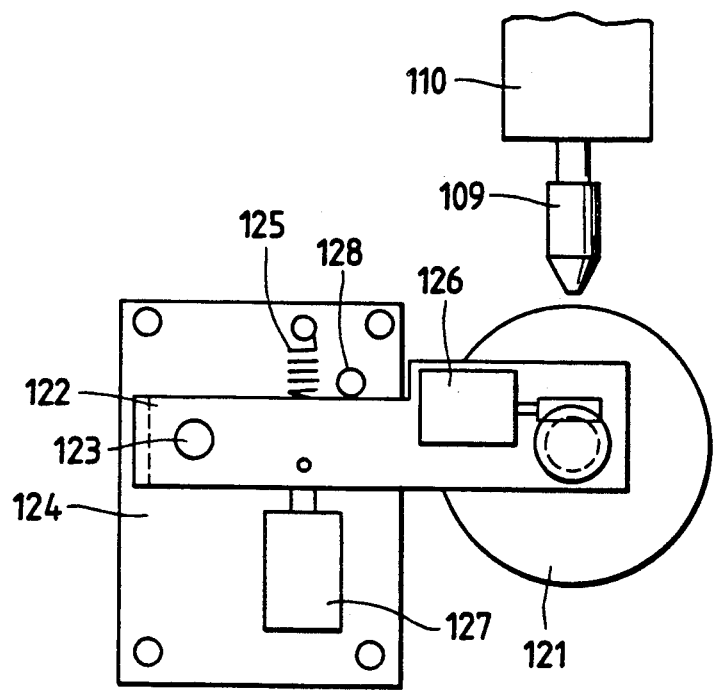
FIG. 8(a) is a front view of a support member that is provided on the periphery of a disk-shaped support and on which the components of a sample to measured are successively deposited as they ar separated by a liquid chromatography.
Figure 8B:
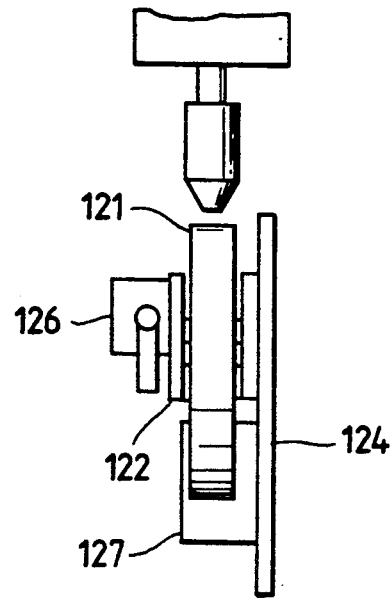
FIG. 8(b) is a side view of the apparatus shown in FIG. 8(a)

FIGS. 8(a) and 8(b) are a front view and a side view, respectively, that show a support member that is provided on the periphery of a disk-shaped support and on which the components of a sample to be measured are successively deposited as they are separated by the liquid chromatography. Referring to FIG. 8(a), numeral 121 represents a disk that is elastic at least in the surface layer of its periphery, and 122 is an arm that is made of a U-shaped plate member. The disk 121 is inserted between the legs in the right end portion of the arm 122 (see FIG. 8(b)) and is supported rotatably between those legs. The left end portion of the arm 122 is rotatably supported about a pin 123 erected on a substrate 124.

A motor 126 is secured to the surface of the leg of the arm 122 as shown on the left side of FIG. 8(b) and drives the disk 121 to rotate via a worm and a wormwheel (not labelled with numerals). An actuator 127 is coupled to the arm 122 and drives the latter to rotate clockwise about pin 123. The arm 122 is urged by spring 125 to rotate counterclockwise about pin 123 until it contacts a stopper 128 so that it will stop its further movement.

A nozzle 109 connected to the outlet of column 110 is positioned above the disk 121 in proximity to its peripheral surface. Components of the sample separated in the column 110 are discharged through the nozzle 109 at a given speed together with the mobile phase carrier and are successively deposited at different positions on the top of the peripheral surface of the disk 121 being rotated at a constant speed. When each of the components deposited on the peripheral surface of the disk 121 has moved to the lowest point on its peripheral surface as a result of the rotation of the disk, the component is driven to rotate by a small amount about the pin 123 in a clockwise direction by means of the actuator 127, whereupon the component is pressed into intimate contact with the reflecting face of the prism (not shown). Prior to the pressing operation, the mobile phase carrier is evaporated to leave only the component of interest intact on the peripheral surface of the disk.

Figure 9A:
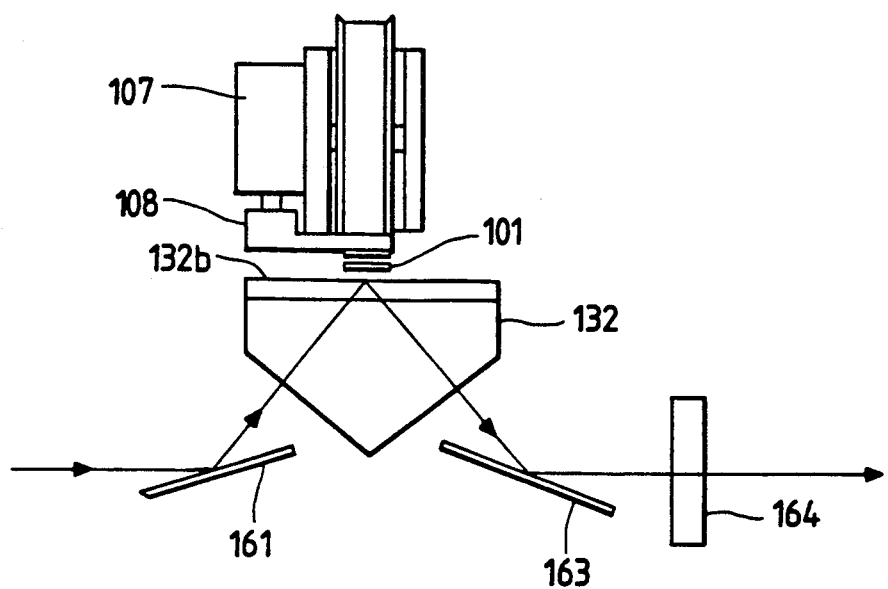
FIG. 9(a) is a front view of a modification of the prism used in the apparatus of the present invention.
Figure 9B:
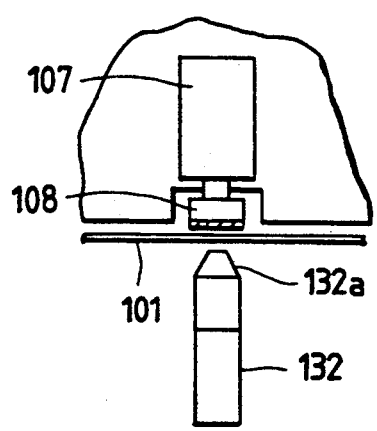
FIG. 9(b) is a side view of the apparatus shown in FIG. 9(a)
Figure 9C:
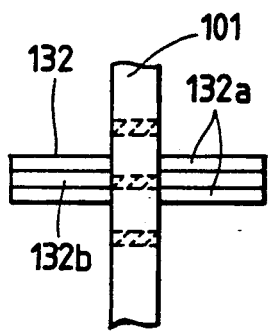
FIG. 9(c) is a partial plan view of the apparatus shown in FIG. 9(a)

FIGS. 9(a), 9(b) and 9(c) are a front view, a side view and a partial plan view, respectively, of a modification of the prism used in the infrared absorption enhanced spectroscopic apparatus of the present invention. The infrared spectrometer shown in FIG. 9(a) differs from the apparatus shown in FIG. 1 with respect to the shape of the reflecting face of the prism. As shown in FIGS. 9(a) and 9(b), the prism indicated by 132 is chamfered on the edges of sides 132a that are parallel to planes including incident and exit light and, as a result of this chamfering, the width of the reflecting face 132b becomes smaller than in the case where no such chamfering is effected.

The purpose of chamfering side edges of the prism is to have incident infrared light focused in the narrow area of the reflecting face 132b and to insure exact correspondence between the width of the reflecting face and the narrow band of each component separated by the liquid chromatography, thereby improving the sensitivity or S/N ratio of detecting the separated components by infrared spectroscopy. In FIGS. 9(a) and 9(b), the tape 101 in the device having the separated components of the sample deposited at different positions is placed in close proximity to and transverse to the width of the outer surface of the reflecting face 132b of the prism 132. The individual separated components of the sample are deposited at different positions on the surface of the tape 101 just above the reflecting face 132b. As shown in FIG. 9(c), the separated components on the tape 101 are spaced apart to form bands or islands as indicated by dashed lines, the width of each band being measured along the length of the tape. Since the amount of each component separated from the sample is inherently small, it is effective for the purpose of improving the detection sensitivity or S/N ratio to minimize the width of the band while maximizing its thickness.

Figure 10A:
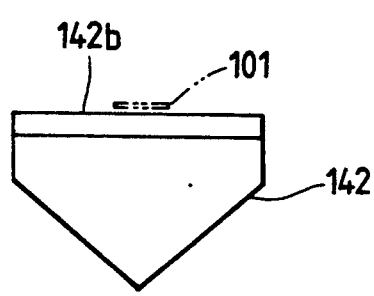
FIG. 10(a) is a front view of another modification of the prism used in the apparatus of the present invention.
Figure 10B:
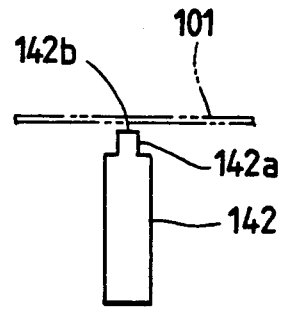
FIG. 10(b) is a side view of the apparatus shown in FIG. 10(a).

FIGS. 10(a) and 10(b) are a front and a side view, respectively, of another modification of the prism used in the infrared absorption enhanced spectroscopic apparatus of the present invention. As shown in FIG. 10(b), the edges of two sides 142a of the prism 142 are cut off to produce a narrowed reflecting face 142b. Whether the edges of prism sides should be chamfered or cut off depends chiefly on the dimensional precision in narrowing the reflecting face of the prism and the type of machining tool used.

For detecting the separated components, the actuator 107 and hence the compression block 108 are operated so that they are pressed into intimate contact with the outer surface of the reflecting face 16b, 132b or 142b. The reliability of this pressing operation is insured by the flexibility of the tape 101. The device shown in FIG. 6 may be used as an accessory to the infrared spectrometer for separating the sample into components and performing spectroscopic analysis in a continuous manner.

Alternatively, the infrared spectrometer may be installed in a convenient place and, when necessary the device shown in FIG. 6 is detached and brought into that place for performing spectroscopic analysis.

The device shown in FIG. 7 is not suitable for use in the continuous operation described above. In all situations, the infrared spectrometer is installed in a convenient place and the device shown in FIG. 7 is detached and brought into that place for performing spectroscopic analysis. In this case, the device is not used in the attitude shown in FIG. 7 but is turned upside down before i is combined with the infrared spectrometer. The tape 111 is also flexible, so as in the device shown in FIG. 6, the separated components of the sample can be positively pressed into intimate contact with the outer surface of the reflecting face 16b, 132b or 142b of the prism 16, 132 or 142, respectively.

Like the device shown in FIG. 6, the device shown in FIG. 8 can be used either as an accessory to the infrared spectrometer or as a separate element to be attached thereto as required. Further, the disk 121 is elastic at least in the surface layer of its periphery, so the separated components of the sample can again be positively pressed into intimate contact with the outer surface of the reflecting face 16b, 132b or 42b of the prism 16, 132 or 142, respectively.

As described on the foregoing pages, the present invention has the advantage of providing an infrared absorption enhanced spectroscopic apparatus that permits a metal surface, an overlying thin layer of sample and a-high refractive-index prism to be readily set in such a way that their relative positions can be measured, that permits the angle of incident infrared light to be readily adjusted in such a way that the wave number of infrared light travelling through the prism in a direction parallel to its bottom surface becomes equal to the wave number of surface electromagnetic waves to be excited, and that has an optical system which causes a sufficiently small loss of infrared light to achieve a satisfactory S/N ratio.

The foregoing description of preferred embodiments of the invention has been presented for purposes of illustration and description. It is not intended to be exhaustive or to limit the invention to the precise form disclosed. Modifications and variations are possible in light of the above teachings or may be acquired from practice of the invention. The embodiments were chosen and described in order to explain the principle of the invention and its practical application to enable one skilled in the art to utilize the invention in various embodiments and with various modifications as are suited to the particular use contemplated. It is intended that the scope of the invention be defined by the claims appended hereto and their equivalents.

What is claimed is:

1. A method for analyzing a sample layer in an infrared absorption enhanced spectroscopic apparatus with an incident infrared light, comprising the steps of:
   preparing a flexible support member;
   providing a metal layer overlaying said support member;
   depositing the sample layer on said metal layer;
   providing a prism means for redirecting the incident infrared light, having a reflecting surface and opposing entrance and exit surfaces configured to minimize a divergence of the incident infrared light;
   positioning said flexible support member and said metal layer with the sample layer contacting said reflecting surface of said prism means with a uniform pressure; and
   adjusting the incident light with an adjusting means for adjusting an angle of incidence of the incident infrared light with respect to said reflecting surface of said prism means.

2. The method of claim 1, wherein the adjusting step includes a substep of adjusting the angle of incidence of the incident infrared light to focus said incident infrared light on the sample layer contacting said reflecting surface of said prism means.

3. The method of claim 1, wherein the step of providing a flexible support member includes providing a support member which is also elastic.

4. The method of claim 1, wherein the step of providing a flexible support member includes providing a support member including one plastic material selected from the group consisting of polyethylene terephthalate and polyester.

5. The method of claim 1, wherein said step of providing the metal layer includes providing a metal layer including a solid plasma of aluminum.

6. The method of claim 1, wherein said opposing entrance surface and exit surface intersect said reflecting surface of said prism means to define edges, and further including the step of chamfering at least one of said edges.

7. The method of claim 6, wherein said chamfering step includes chamfering said at least one edge to reduce a surface area of said reflecting surface to correspond to a surface area of the sample layer.

8. The method of claim 1, wherein the step of providing a support layer includes providing an elongated tape having a selected length, alternately wound on one of a pair of rotatable reels.

9. The method of claim 8, wherein the metal layer is provided overlaying said elongated tape, and the step of depositing the sample layer includes depositing a plurality of sample layer portions at selected positions along the length of the tape.

10. The method of claim 9, wherein the step of positioning the flexible support layer and metal layer includes a substep of using a tape holding and transporting means for rotating the reels and moving the tape along the reflection surface at a predetermined speed.

11. The method of claim 1, wherein the step of providing a support member includes providing a disk shaped support member rotatable around a longitudinal axis.

12. An infrared absorption enhanced spectroscopic apparatus for analyzing a sample layer with an incident infrared light, comprising:
   a flexible support member;
   a metal layer deposited overlaying said support member, the sample layer being deposited on said metal layer;
   prism means for redirecting the incident infrared light, including a reflecting surface and opposing entrance and exit surfaces, said entrance surface and exit surface configured to minimize a divergence of the incident infrared light;
   positioning means for positioning said flexible support member and said metal layer with the sample layer in contact with said reflecting surface of said prism means with a uniform pressure; and
   adjusting means for adjusting an angle of incidence of the incident infrared light with respect to said reflecting surface of said prism means.

13. The apparatus of claim 12, wherein said adjusting means includes a first reflector pivotally mounted with respect to the entrance surface, and a second reflector pivotally mounted with respect to the exit surface.

14. The apparatus of claim 13, wherein said first and second reflectors are pivotable to a selected position to focus the incident infrared light on the sample layer contacting said reflecting surface of said prism means.

15. The apparatus of claim 12, wherein said opposing entrance and exit surfaces intersect said reflecting surface to define edges, at least one of said edge being chamfered, defining said reflecting surface having a surface area corresponding to a surface area of the sample layer.

16. The apparatus of claim 12, wherein said support layer includes an elongated tape member having a selected length alternately wound between a pair of rotatable reel members.

17. The apparatus of claim 16, wherein said metal layer is deposited on said tape member, and the sample layer includes a plurality of sample layer portions deposited at a plurality of positions along the selected length.

18. The apparatus of claim 16, further including tape holding and transporting means for moving the tape member along said reflecting surface at a predetermined speed.

19. The apparatus of claim 12, wherein said support member includes a peripheral surface of a disk-shaped member rotatable around a longitudinal axis.

* * * * *